United States Patent [19]

Varco et al.

[11] Patent Number: 4,913,893

[45] Date of Patent: Apr. 3, 1990

[54] AEROSOL HAIR SETTING COMPOSITION CONTAINING AN ALGINATE

[75] Inventors: Joseph J. Varco, Fairfield; Gabriela M. Wis-Surel, Milford; Janusz Jachowicz, Bethel, all of Conn.

[73] Assignee: Clairol Incorporated, Stamford, Conn.

[21] Appl. No.: 90,642

[22] Filed: Aug. 28, 1987

[51] Int. Cl.⁴ ................................................ A61K 7/11
[52] U.S. Cl. ........................................ 424/47; 424/70; 424/71; 424/DIG. 1
[58] Field of Search ..................... 424/71, DIG. 1, 44, 424/70, 47; 514/880, 944–945

[56] References Cited

U.S. PATENT DOCUMENTS 4,673,569  6/1987  Shernov et al. .............. 424/DIG. 1

FOREIGN PATENT DOCUMENTS 1017843  1/1964  United Kingdom .................. 424/71
1036497  7/1966  United Kingdom .................. 424/71

OTHER PUBLICATIONS

Bergwein, Karl: "Foaming Agents in Cosmetics," *Drug and Cosmetic Industry*, p. 163, Aug. 1957.

Primary Examiner—Ellis P. Robinson
Assistant Examiner—P. L. Prater
Attorney, Agent, or Firm—Charles J. Zeller

[57] ABSTRACT

An aqueous aerosol composition containing an alginate that is useful as a hair setting mousse.

9 Claims, No Drawings

AEROSOL HAIR SETTING COMPOSITION CONTAINING AN ALGINATE

This invention relates to hair setting compositions of the type that is dispensed from an aerosol can and are commonly referred to in this art as mousses. More particularly it concerns the use of alginates in such a hair setting compositions. Formulas containing alginates have been known in the prior art as exemplified by the GB Patent 1036497 to Schwarzkopf, granted in 1966. These compositions were primarily aqueous systems containing the alginate. When such compositions were applied to hair and dried they provided hairsetting effects. In this form, however, it was difficult and inconvenient to apply such products to the head.

More recently, hairsetting compositions have taken the form of hair sprays that utilize synthetic polymers as the active ingredient. These compositions were generaly prepared using alcohols as the principal vehicle, but because of their incompatibility with alcohols the alginates have not been used in such hairspray compositions.

It has now been found that compositions containing alginates when incorporated in a mousse form aersol product are excellent hair conditioning and/or hair setting compositions. The products used in this fashion not only provide an easy and controllable method of application but the non-sticky quality of the alginate film that is deposited on the hair offers unique advantages over the synthetic polymer resin compositions.

A number of alginates are known in the prior art which are useful for the purposes of this invention. These alginates usually take the form of salts or esters of alginic acid the preferred alginates being the alkali metal or alkaline earth metal alginates and particularly sodium alginate. By way of example of the alginates that may be employed in the present invention mention is made of the following:

Sodium alginate, potassium alginate, ammonium alginate, propylene glycol alginate and ethylene glycol alginate.

The products of the present invention are made up by first formulating a concentrate containing the alginate which is then mixed with a propellent system and filled into aerosol cans. The principle carrier for the concentrate will generally be an aqueous carrier which may comprise water or a combination of water with other solvents. To illustrate the solvents that may be employed along with the water to form the aqueous carrier, mention may be made of the following:

ethanol (up to 20% in $H_2O$-ethanol mixture), isopropanol (up to 20% in $H_2O$-isopropanol mixture) and benzyl alcohol (up to 20% in $H_2O$-benzyl alcohol mixture).

The quantity of alginate that may be contained in the concentrate may be varied depending upon the results desired and in the economics involved. Generally the alginate will be present in the concentrate at a concentration in a range of from about 0.1% to about 10% by weight based on the total weight of the concentrate and depending on the molecular weight of the polymer. In the preferred forms of this invention the alginate will constitute between about 0.50 to about 3.00% by weight based on the total weight of the concentrate.

To formulate the present compositions as a mousse one or more foaming aids is incorporated in the concentrate. Illustrative of the foaming aids that are useful in the practice of the present invention mention may be made of the following:

sodium, ammonium or triethanolamine lauryl sulfate; polyethylene glycol ether fatty alcohols (20–45 moles of ethoxylation), sodium isethionate, sodium lauroyl sarcosinate, and sodium and ammonium xylene sulphonate.

The total quantity of foaming aids that may be incorporated in the concentrates of this invention will vary somewhat. Usually this will comprise about 0.1% to about 1.8% by weight based on the total weight of the concentrate with the preferred range being from about 0.2% to about 1.0% on the same weight basis.

In addition to the alginate and foaming agents in the present concentrate there may be also be incorporated therein any of a number of adjuvants commonly found in mousse preparations. These are added to facilitate the application of the product, to provide chemical or physical stability or to add to the organoleptic properties of the product. By way of example of such adjuvants mention may be made of preservatives (methyl paraben, dibasic potassium phosphate, dibasic sodium phosphate, sodium benzoate, potassium sorbate, calcium propionate, sodium propionate, heximinium salts, 2-phenoxyethanol. Water-soluble and alginate-compatible synthetic or natural polymers (neutral, anionic or amphoteric) may be used for the improvement of film properties, viscosity adjustments etc. Poly (vinyl alcohol), poly (vinylpyrrolidone), poly (styrene sulphonate), poly (acrylic acid), poly (methacrylic acid), carboxymethylcellulose, hydroxyethylcellulose, hydroxypropylcellulose, carboxymethylchitin, copolymers of methyl vinyl ether and maleic anhydride are examples of high molecular weight compounds that can be employed to plasticize the alginate film, reduce powdering or to improve adhesion between the alginate film and hair surface. Low molecular weight compounds such as propylene glycol, ethylene glycol, hexylene glycol, glycerol, triethanolamine can also be utilized as plasticizers.

As indicated above, it is a feature of the present invention to formulate the compositions of this invention as aerosol products to be dispensed from an aerosol can. For this purpose a propellent system is employed. A number of propellents used singularly or in combination well known in the aerosol art may be used for the present purposes. By way of example, mention may be made of the following:

Hydrofluorocarbon 152A ($CH_3CHF_2$), Isobutane and dimethyl ether.

The propellents outlined above may be used alone or in combination in various ratios. A particularly useful propellent system is a combination of Hydrofluorocarbon 152A and Isobutane. These are preferably used in the ratio of 80:20 to 60:40 of Hydrofluorocarbon 152A to Isobutane.

In preparing the aerosol mousse products of this invention the concentrate and propellent system may be charged into the aerosol can in proportions that vary over range. These aerosols will generally comprise from about 3% to about 25% by weight of propellant based on the total weight of the aerosol composition the balance being made up by the concentrate. In the preferred form of this invention the aerosol mousse product will contain from about 3% to about 15% of propellant on the same weight basis.

It is also useful to sometimes express the concentration of the various components of the products here of interest on the basis of the total weight of the aerosol composition; that is the finished composition in the aerosol can which contains both the concentrate and the propellant system. With this in mind the following table is presented:

TABLE

| Ingredient | General % w/w based on total weight of aerosol product | Preferred % w/w based on total weight of aerosol product |
| --- | --- | --- |
| Alginate | from about 0.1% to about 9% | from about 0.45% to about 2.7% |
| Foaming Aid | from about 0.1% to about 1.8% | from about 0.18% to about 0.9% |
| Propellant | from about 3% to about 25% | from about 3% to about 15% |
| Aqueous Vehicle + Adjuvants (if any) | Qs to 100% | Qs to 100% |

The mousse products of the present invention are evaluated for curl holding ability by their application to hair under controlled conditions. Curl relaxation is then measured on exposure to high humidity and compared with appropriate standards. For example, 0.3 g of mousse product is applied and spread throughout a 2 g swatch of hair. The hair tress is curled on a mandrel and dried at ambient conditions. Curl relaxation that consists of periodic measurement of the curl fall, is then performed under exposure to high humidity (90-95% R.H.)

The following examples are given to further illustrate the present invention. It is understood however that this invention is not limited thereto.

The procedure used in preparing the products shown in Examples 1-5 is the same. All the ingredients listed under the heading "Concentrate" are mixed together to form the concentrate. This concentrate is then charged into an aerosol can which is sealed with a cover having a valve and valve stem assembly. The propellant system is then introduced into the sealed can under pressure through the valve stem.

EXAMPLE 1

| (A) Concentrate | % w/w |
| --- | --- |
| Sodium Alginate | 1.5 |
| Isosteareth 10 | 0.2 |
| Sodium isethionate | 0.25 |
| Methyl paraben | 0.10 |
| 2-phenoxyethanol | 0.20 |
| Fragrance | q.s. |
| Deionized Water | q.s. to 100.00% |
| (B) Aerosol Composition | % w/w |
| Above concentrate | 92.0 |
| Hydrofluorocarbon 152A/ Isobutane (75:25) | 8.0 |

The performance of the product with a composition described above offers a long lasting hold effect to the hair as well as an excellent, non-tacky film quality.

Examples 2-4 illustrate the use of alginates in combination with other water-soluble polymers.

EXAMPLE 2

| (A) Concentrate | % w/w |
| --- | --- |
| Sodium Alginate | 0.75 |
| Gantrez 225* | 0.75 |
| Isosteareth 10 | 0.20 |
| Sodium isethionate | 0.25 |
| Methyl paraben | 0.10 |
| 2-phenoxyethanol | 0.20 |
| Fragrance | q.s. |
| Deionized Water | q.s. 100.00% |
| (B) Aerosol Composition | % |
| Above concentrate | 92.0 |
| Hydrofluorocarbon 152A/ Isobutane (75:25) | 8.0 |

*monoalkyl ester of Poly(methylvinylether/maleic acid)

EXAMPLE 3

| (A) Concentrate | % w/w |
| --- | --- |
| Sodium Alginate | 0.75 |
| Poly (vinyl pyrrolidone) | 0.75 |
| Isosteareth 10 | 0.20 |
| Sodium isethionate | 0.25 |
| Methyl paraben | 0.10 |
| 2-phenoxyethanol | 0.20 |
| Fragrance | q.s. |
| Deionized Water | q.s. to 100.00% |
| (B) Aerosol Composition | % w/w |
| Above concentrate | 92.0 |
| Hydrofluorocarbon 152A/ Isobutane (75:25) | 8.0 |

EXAMPLE 4

| (A) Concentrate | % w/w |
| --- | --- |
| Sodium Alginate | 0.75 |
| Carboxymethylchitin | 0.75 |
| Isosteareth 10 | 0.20 |
| Sodium isethionate | 0.25 |
| Methyl paraben | 0.10 |
| 2-phenoxyethanol | 0.20 |
| Fragrance | q.s. |
| Deionized Water | q.s. to 100.00% |
| (B) Aerosol Composition | % w/w |
| Above concentrate | 92.0 |
| Hydrofluorocarbon 152A/ Isobutane (75:25) | 8.0 |

Example 5 illustrates the use of propylene glycol alginate in a mousse composition.

EXAMPLE 5

| (A) Concentrate | % w/w |
| --- | --- |
| Propylene glycol alginate | 1.5 |
| Isosteareth 10 | 0.20 |
| Sodium isethionate | 0.25 |
| Methyl paraben | 0.1 |
| 2-phenoxyethanol | 0.2 |
| Fragrance | Q.S. |
| Deionized Water | Q.S. to 100.00% |
| (B) Aerosol Composition | % w/w |
| Above concentrate | 92.0 |
| Hydrofluorocarbon 152A/ Isobutane (75:25) | 8.0 |

What is claimed is:

1. An aerosol composition contained in an aerosol can and useful for conditioning and/or setting hair comprising by weight of the aerosol composition:
    (a) from about 0.1% to about 9% of an alginate selected from the group consisting of ammonium alginate, ethylene glycol alginate and propyleneglycol alginate,
(b) from about 64.2% to about 96.8% of an aqueous carrier,
(c) from about 0.1% to about 1.8% of a foaming aid component, and
(d) from about 3% to about 25% of a propellent system, said composition producing a mousse when dispensed from the aerosol can.

2. A composition according to claim 1 wherein said alginate comprises from about 0.45% to about 2.70% by weight based the total weight of said aerosol composition.

3. A composition according to claim 1 wherein said foaming aid component comprises from about 0.18% to about 0.9% by weight based on the total weight of said aerosol composition.

4. A composition according to claim 1 wherein said propellent system comprises from about 3.0% to about 15.0% by weight based on the total weight of said aerosol composition.

5. A composition according to claim 1 wherein said aerosol composition contains from about 0.45% to about 2.7% alginate, from about 0.18% to about 0.9% foaming aid component, and from about 3.0% to about 15.0% propellent system.

6. A composition according to claim 5 wherein said foaming component is selected from the group consisting of sodium, ammonium or triethanolamine lauryl sulfate, polyethylene glycol ether fatty alcohols having 20-45 moles of ethoxylation, sodium isethionate, sodium lauroyl sarcosinate, sodium or ammonium xylene sulphonate and mixtures thereof.

7. A process for conditioning and/or setting hair comprising of applying to said hair an effective conditioning and/or setting amount of a composition defined in claim 1, or 6.

8. A composition according to claim 5 further comprising one or more of the following adjuvants: preservative; water-soluble and alginate-compatible polymers as alginate film-property improvers, plasticizers, and fragrance, said adjuvants being present in an amount effective to obtain the functionality thereof.

9. A composition according to claim 5 wherein the aqueous carrier comprises by weight of the carrier up to about 20% of an alcohol selected from ethanol, isopropanol and benzyl alcohols.

* * * * *